United States Patent
Lukay et al.

(10) Patent No.: US 8,739,609 B2
(45) Date of Patent: Jun. 3, 2014

(54) TEST SAMPLE HEATING APPARATUS AND METHOD

(75) Inventors: Richard Lukay, Houston, TX (US); Jarod Hammar, Cypress, TX (US)

(73) Assignee: OFI Testing Equipment, Inc., Houston, TX (US)

( * ) Notice: Subject to any disclaimer, the term of this patent is extended or adjusted under 35 U.S.C. 154(b) by 698 days.

(21) Appl. No.: 12/732,680

(22) Filed: Mar. 26, 2010

(65) Prior Publication Data

US 2010/0242577 A1    Sep. 30, 2010

Related U.S. Application Data

(60) Provisional application No. 61/164,161, filed on Mar. 27, 2009.

(51) Int. Cl.
   *G01N 11/00* (2006.01)

(52) U.S. Cl.
   USPC .................. 73/54.43; 73/75.38; 73/54.28

(58) Field of Classification Search
   USPC .......... 73/54.28–54.35, 54.42, 54.43, 863.11, 73/54.37–54.39
   See application file for complete search history.

(56) References Cited

U.S. PATENT DOCUMENTS

| | | | |
|---|---|---|---|
| 2,703,006 A * | 3/1955 | Savins | 73/54.33 |
| 3,262,494 A * | 7/1966 | Smith, Jr. | 165/104.31 |
| 3,435,666 A * | 4/1969 | Fann | 73/54.39 |
| 5,616,855 A | 4/1997 | Ball | |
| 5,696,315 A | 12/1997 | Ball | |
| 6,571,610 B1 | 6/2003 | Raffer | |
| 6,698,275 B2 * | 3/2004 | Hall | 73/54.28 |
| 6,708,554 B2 * | 3/2004 | Hettwer et al. | 73/54.43 |
| 7,168,299 B2 * | 1/2007 | Doe et al. | 73/54.43 |
| 7,367,224 B2 | 5/2008 | Platzek et al. | |
| 8,230,723 B2 * | 7/2012 | Moon et al. | 73/54.28 |
| 2003/0056575 A1 | 3/2003 | Hettwer et al. | |
| 2004/0026403 A1 * | 2/2004 | Kariya et al. | 219/444.1 |
| 2005/0199044 A1 | 9/2005 | Doe et al. | |
| 2009/0145207 A1 * | 6/2009 | Bousmina et al. | 73/61.61 |

OTHER PUBLICATIONS

AMETEK, Chandler Engineering brochure for Model 5550 HPHT Viscometer, submitted May 21, 2010.

* cited by examiner

*Primary Examiner* — Hezron E Williams
*Assistant Examiner* — Hoang Nguyen
(74) *Attorney, Agent, or Firm* — Keeling Patents & Trademarks, LLC; Kenneth A. Keeling; Melissa M. Martinez

(57) ABSTRACT

A test sample heating apparatus and method includes a heating jacket that applies heat to a sample vessel containing a test sample. The heating jacket has a vessel-receiving recess that is sized and shaped to allow the sample vessel to be placed within the recess with limited annular spacing between at least part of the sample vessel exterior surface and at least part of the heating jacket recess interior surface. Proximate surfaces of at least one of the heating jacket and the sample vessel may be coated with a dark coating to enhance heat transfer.

16 Claims, 2 Drawing Sheets

TEST SAMPLE HEATING APPARATUS AND METHOD

CROSS-REFERENCE TO RELATED APPLICATIONS

This application claims the benefit of U.S. Provisional Application No. 61/164,161 filed on Mar. 27, 2009, which application is incorporated herein by reference as if reproduced in full below.

STATEMENT REGARDING FEDERALLY SPONSORED RESEARCH OR DEVELOPMENT

Not applicable.

FIELD OF THE DISCLOSURE

This invention relates generally to testing equipment used to measure properties of materials and chemical systems, and more specifically to a heating device used to heat media contained in a sample vessel during material testing.

BACKGROUND

In the oil and gas industry, it is imperative to know and understand the material properties of compositions used during drilling and exploration and to determine how these properties are affected by temperature, pressure and time. Various tests require that a material, compound or formulation, be subjected to testing at temperatures above ambient temperature.

An exemplary material test utilizes a viscometer to determine the viscosity of a fluid sample wherein a sample is rotated in relation to an immersed sensor element such as a bob. It is often desirable to conduct such measurements at above-ambient temperatures.

To do this, the sample is routinely placed in a sample cup having specified dimensions. During testing the sample is arranged within a heating unit with a bob of specified dimension located in the sample cup. Typically, an oil-based or water-based fluid is retained in the heating unit intermediate the heating unit interior surfaces and the sample vessel exterior surfaces to provide efficient heat transfer from the heating unit to the sample vessel and consequently to the sample.

The heating unit typically has an insulating chamber to limit heat dissipation to the environment.

Conventional heating units for instruments that test fluid properties typically comprise a container constructed to hold a liquid heating medium, typically an oil. Heaters are used to apply heat to the heating unit's retaining wall which is in direct contact with the heating liquid, thus increasing the liquid's temperature. The sample vessel is at least partially surrounded by the liquid inside the heating jacket. The liquid imparts heat to the sample vessel through conduction heating. In this system, the retaining surface of the heating unit is typically machined aluminum and the exterior surface of the sample vessel is a corrosion-resistant alloy.

A second conventional heating apparatus uses a machined graphite block to replace the oil. The graphite block is machined to directly contact the outer surfaces of the sample vessel. Heaters apply heat directly to the graphite block, which increases the block's temperature. An exemplary heating apparatus using graphite block is marketed by Chandler Engineering as Model No. 5550 HPHT Viscometer.

BRIEF SUMMARY OF THE DISCLOSURE

A test sample heating apparatus and method includes a heating jacket that applies heat to a sample vessel containing a test sample. The heating jacket has a vessel-receiving recess that is sized and shaped to allow the sample vessel to be placed within the recess with limited annular spacing between at least part of the sample vessel exterior surface and at least part of the heating jacket recess interior surface. Proximate surfaces of at least one of the heating jacket and the sample vessel may be coated with a dark coating to enhance heat transfer.

BRIEF DESCRIPTION OF THE DRAWINGS

For a more complete understanding of the exemplary embodiments, reference is now made to the following Description of Embodiments of the Invention, taken in conjunction with the accompanying drawings, in which.

DESCRIPTION OF EXEMPLARY EMBODIMENTS OF THE INVENTION

Figure 1:
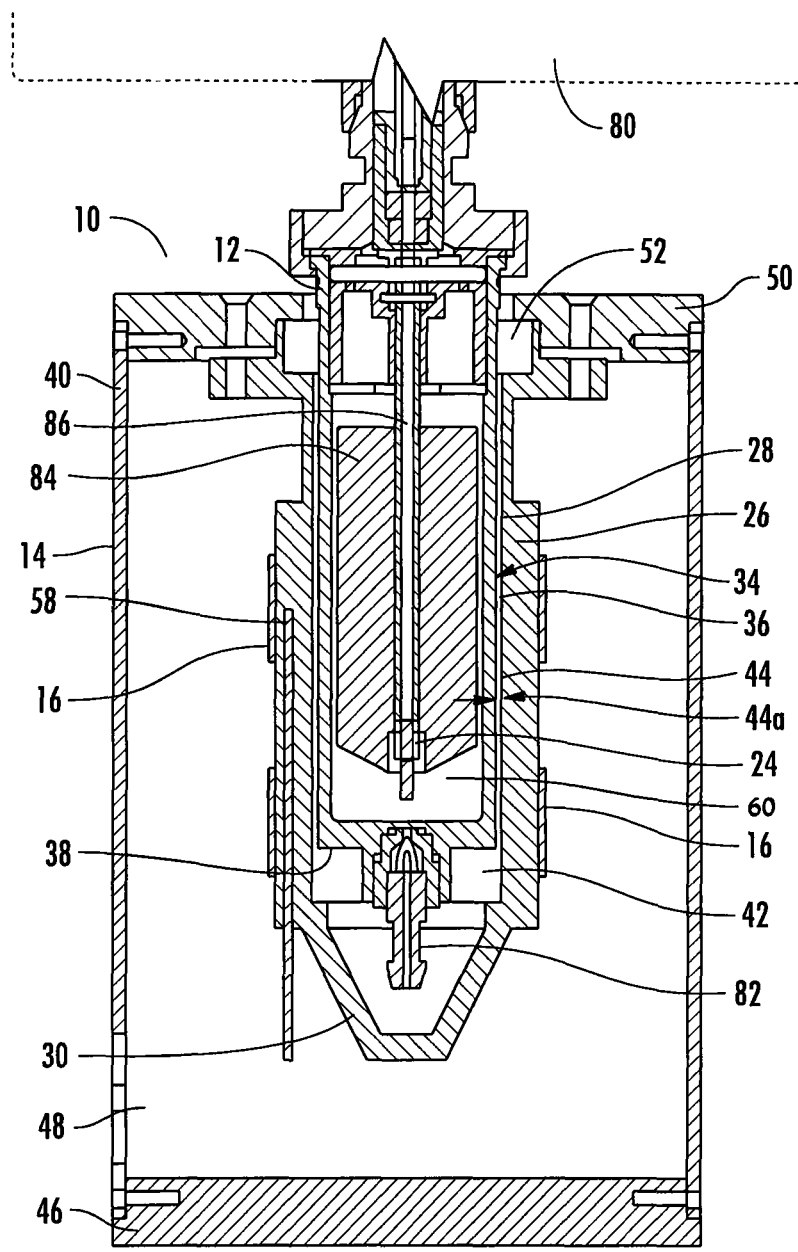
FIG. 1 shows a cross section of an embodiment of a sample vessel and a heating unit.

The exemplary embodiment is best understood by referring to the drawings, like numerals being used for like and corresponding parts of the various drawings.

The directions lower and upper as used in this specification are used for descriptive purposes only and it will be understood by one having skill in the art that different orientations are possible.

Referring to FIG. 1, a cross-sectional view of a test sample heating apparatus 10 is shown.

An exemplary sample cup 12 is shown positioned in a heating unit 14. More particularly, sample cup 12 is positioned in heating unit recess 42 of heating unit 14.

Sample cup 12 comprises a generally cylindrical cup having a sample wall 34 and a sample cup bottom 38. In the embodiment depicted, sample cup 12 is attached to a viscometer 80 by conventional attachment means. A stem valve 82 extends from sample cup bottom 38. A viscometer bob 84 extends into sample cup 12. Viscometer bob 84 is attached to viscometer 80 by means of bob shaft 86.

Heating unit 14 generally comprises a heat jacket 26 disposed within an exterior heat shield 40, an exterior base 46 and a lid 50. Heat jacket 26 is attached to lid 50 and extends downwardly from lid 50. Insulation 48 is provided intermediate heat jacket 26 and exterior heat shield 40, exterior base 46 and lid 50.

Heat jacket 26 is generally constructed as a hollow cylinder with an open upper end 52 and a closed base 30. Interior wall surface 28 of heat jacket 26 is generally cylindrical from base 30 to upper end opening 52. Interior wall surface 28, base 30 and opening 52 define heating unit recess 42.

Figure 2:
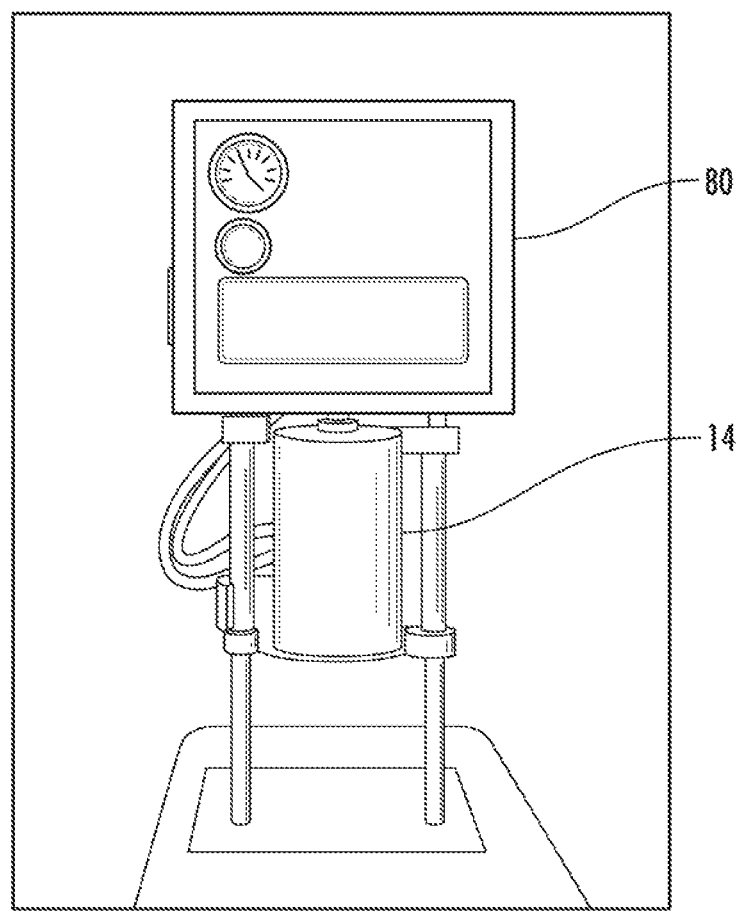
FIG. 2 shows the sample vessel and heating unit of FIG. 1 in relation to a viscometer.

Referring to FIG. 1 and FIG. 2, sample cup 12 is shown in operational placement with sample cup 12 (not visible in FIG. 2) disposed within heating unit recess 42 of heat jacket 26. Sample cup 12 is readily removable from heating unit 14. In the embodiment depicted such removal may be accomplished by lowering heating unit 14 in relation to viscometer 80.

Heating elements 16 are attached to heat jacket 26. Heating elements 16 comprise heater bands extending around heat jacket 26. Heating elements 16 are electrically connected to a power source (not shown). Heat regulation is provided by a controller (not shown), which may be computer-controlled.

Thermocouple 24 is provided for measurement of temperature interior of sample cup 12. In the embodiment depicted, thermocouple 24 is contained within bob shaft 86. Thermocouple 58 is provided in heat jacket 26 for measurement of temperature of heat jacket 26.

Sample cup 12 wall 34 has an exterior surface 36. Heat jacket 26 has an interior wall surface 28. Sample cup 12 is closely received within heating unit recess 42 of heat jacket 26 with an annular opening 44 defined by sample cup exterior surface 36 and jacket interior wall surface 28.

Heating unit recess 42 is sized to allow insertion and removal of sample cup 12 into and from heating unit recess 42 of heating unit 14. Sample cup 12 and heating unit 14 are structured and sized to limit the lateral dimension 44a of annular opening 44. Lateral dimension 44a is the distance between sample cup exterior surface 36 and jacket interior wall surface 28.

In an exemplary embodiment, sample cup 12 and heating unit 14 are constructed such that annular opening lateral dimension 44a between sample cup exterior surface 36 and jacket interior wall surface 28 is in a range of 0.127 mm (0.005 inches) to 6.35 mm (0.25 inches) with sample cup 12 installed in heating unit recess 42. Such limited annular opening enhances radiant heat transfer between sample cup exterior surface 36 and jacket interior wall surface 28.

In an exemplary embodiment emissivity of sample cup exterior surface 36 is increased by applying a coating 54 to sample cup wall exterior surface 36. In an exemplary embodiment, cup coating 54 is a material having an emissivity coefficient in the range of 0.6 to 1.0. A coating 54 having an emissivity coefficient of greater than 0.9, such as black paint, is preferred.

In an exemplary embodiment, cup coating 54 is a non-reflective material such as a flat paint or a matte paint.

In an exemplary embodiment emissivity of jacket interior wall surface 28 is increased by applying a coating 56 to heating unit recess 42 interior wall surface 28. In an exemplary embodiment, coating 56 is a material having an emissivity coefficient in the range of 0.6 to 1.0. A coating 56 having an emissivity coefficient of greater than 0.9, such as black paint, is preferred. In an exemplary embodiment, coating 56 is a non-reflective material such as flat paint or matte paint.

In exemplary tests of test sample heating apparatus 10, a sample cup 12 containing a sample material 60 comprising water was placed in a heating unit 14. Sample cup coating 54 and heating unit coating 56 each comprised a low-reflectivity flat black coating. Annular opening 44a comprised a measured distance of 1.27 mm (0.050 inches) in one test and 3.175 (0.125 inches) in another test. Heating elements 16 were activated to increase temperature of heating unit recess 42 interior wall surface 28 in a range starting at ambient temperature of 21° C. (70° F.) and extending upward to 177° C. (350° F.). Temperature readings were regularly taken at thermocouple 24. Temperature readings were regularly taken at thermocouple 58.

It was determined that heat transfer from heating unit 14 to sample cup 12 was adequate to provided controlled temperature within the described temperature range with acceptable time differential between the measured temperature of sample material 60 and heating unit recess 42 interior wall surface 28.

It was further determined that the achievement of a desired temperature of the test sample and maintenance of a desired temperature of the test sample was enhanced in the present invention as compared to a conventional application using a fluid heating medium within heating unit recess 42. An apparent reason for improved control is reduced thermal mass of the present invention in the heating unit recess 42 resulting from elimination of the liquid heat transfer medium. In a conventional application, the liquid medium is heated to transfer heat to the test sample within sample cup 12. When a desired temperature is achieved and heating elements 16 are deactivated, a liquid medium continues to transfer heat to the sample cup 12. The present invention does not eliminate continued heat transfer between heating unit recess 42 interior wall surface 28 and sample cup wall exterior surface 36 upon deactivation of heating elements 16. However, the present invention, having less thermal mass and having annular opening 44, responds more quickly to decrease heat transfer when heating elements 16 are deactivated.

In operation, the heating effect of the sample cup 12 by the heating jacket 26 is accomplished by radiant heat transfer. Heat transfer by conduction or convection is minimal.

In an application of the present invention involving a viscometer 80, a sample material 60 is placed in sample cup 12. Sample cup 12 is placed in heating unit recess 42 without insertion of a conductive liquid between sample cup wall 34 and heat jacket interior wall surface 28. Sample cup 12 and heating unit 14 are then positioned such that viscometer bob 84 is positioned within sample cup 12 and sample cup 12 is attached to viscometer 80. Sample cup 12 is then rotated with respect to heating unit 14. Power is applied to resistive heating elements 16 with a resulting increase in temperature of heating elements 16 and a corresponding increase of temperature of heating jacket 26. As the temperature of heating jacket 26 increases a temperature differential between heating jacket 26 and sample cup 12 develops. Accordingly, there is a net transfer of electromagnetic radiation to sample cup 12 from heating jacket 26, resulting in heating of sample cup 12 and a resulting heating of the sample material 60. The rate of heat transfer from heating jacket 26 to sample cup 12 is a function of the temperature differential, the surface areas of heating jacket 26 and sample cup 12 and the emissivity coefficients of heating jacket 26 and sample cup 12 or, if a coating 54 or coating 56 is used, the emissivity coefficients of the coating 54 and the coating 56. The temperature of the sample 24 is monitored by thermocouple 24 with such temperature controlled by controlling the temperature of heating jacket 26. Viscometer 80 may be used to determine material sample 60 properties at the various temperatures generated. In an exemplary embodiment, heat jacket 26 comprises aluminum and heating unit recess 42 interior wall surface 28 heat jacket coating 56 comprises black paint having a flat finish.

In an exemplary embodiment, sample cup coating 54 of sample cup 12 exterior surface 36 comprises black paint having a flat finish.

In an exemplary embodiment, sample cup 12 comprises a corrosion-resistant alloy.

In an exemplary embodiment, sample cup 12 may be utilized without a coating 54 or heat jacket 26 may be utilized without a coating 56. In either such event, the teachings of the present invention apply, but with a reduction in the heat transfer rate.

In an exemplary embodiment, the finish roughness of sample cup coating 54 is in the range of 630 to 9,842.5 rms microns (16 to 250 rms micro-inch) (wherein rms means root mean square).

In an exemplary embodiment, the finish roughness of heating unit coating 56 of interior wall surface 28 is in the range of 630 to 9,842.5 rms microns (16 to 250 rms micro-inch) (16 to 250 rms micro-inch).

In an alternative embodiment, heat jacket interior wall surface 28 may be anodized with a black dye applied.

In an alternative embodiment, sample cup coating 54 may comprise a relatively dark, non-reflective coating. In an alternative embodiment, heat jacket interior surface 28 coating 56 may comprise a relatively dark, non-reflective coating.

In an alternative embodiment, sample cup coating 54 and heat jacket 26 may be other than a flat finish.

In an alternative embodiment, sample cup coating 54 may comprise a coating having a friction coefficient in the range of 0.2 to 0.0 to allow for lesser dimension of annular opening 44 while allowing ready insertion and removal of sample cup 12 into and from heating unit recess 42 of heating unit 14. An exemplary coating material comprises polytetrafluoroethylene.

In an alternative embodiment, heating unit coating 56 may comprise a coating having a friction coefficient in the range of 0.2 to 0.0 to allow for lesser dimension of annular opening 44 while allowing ready insertion and removal of sample cup 12 into and from heating unit recess 42 of heating unit 14. An exemplary coating material comprises polytetrafluoroethylene.

Various embodiments will be understood from the foregoing description, and it will be apparent that, although embodiments have been described in detail, various changes, substitutions, and alterations may be made in the manner, procedure and/or details thereof without departing from the spirit and scope or sacrificing any of its material advantages, the forms hereinbefore described being merely exemplary embodiments thereof.

We claim:

1. A viscometer apparatus comprising:
   a viscometer;
   said viscometer having a viscometer body, a sample cup, a bob operable to be positioned in said a sample cup, a bob shaft connecting said bob to said viscometer body;
   a heating unit having a heat jacket;
   said heat jacket defining a heating unit recess;
   said sample cup having a cup exterior wall surface;
   said heat jacket having a jacket interior wall surface;
   an annular space between said sample cup exterior wall surface and said heat jacket interior wall surface, wherein there is no direct physical contact between said sample cup exterior wall surface and said heat jacket interior wall surface;
   said heat jacket operable to emit radiant heat energy to said sample cup; and
   said jacket interior wall surface spaced from said cup exterior wall surface a distance in a range of 0.127 mm (0.0005) inches to 6.25 mm (0.25 inches).

2. The apparatus of claim 1, wherein:
   said heat jacket conducted of a thermally-conductive material;
   a heat source is connected to said heat jacket;
   said heat source operable to increase the temperature of said heat jacket;
   whereby said heat jacket is operable to radiate heat from a jacket interior wall to a sample cup exterior wall.

3. The apparatus of claim 2, wherein:
   said jacket interior wall surface coated with a coating having an emissivity coefficient in a range of 0.60 to 1.00.

4. The apparatus of claim 2, wherein:
   said cup exterior wall surface coated with a coating having an emissivity coefficient in a range of 0.60 to 1.00.

5. The apparatus of claim 2, wherein:
   said jacket interior wall surface coated with a coating having a friction coefficient in a range of 0.2 to 0.0; and
   said cup exterior wall surface coated with a coating having a friction coefficient in a range of 0.2 to 0.0.

6. The apparatus of claim 1, wherein:
   said cup exterior wall surface having a cylindrical structure;
   said jacket interior wall surface defining a hollow cylinder; and
   said sample cup operable to rotate within said heat jacket.

7. A viscometer apparatus comprising:
   a viscometer;
   said viscometer having a viscometer body, a sample cup, a bob operable to be positioned in said a sample cup, a bob shaft connecting said bob to said viscometer body;
   a heating unit having a heat jacket;
   said heat jacket defining a heating unit recess;
   said sample cup having a cup exterior wall surface;
   said heat jacket having a jacket interior wall surface;
   an annular space between said sample cup exterior wall surface and said heat jacket interior wall surface, wherein there is no direct physical contact between said sample cup exterior wall surface and said heat jacket interior wall surface; and
   said heat jacket operable to emit radiant heat energy to said sample cup without use of a conductive liquid.

8. The apparatus of claim 7, wherein:
   said heat jacket constructed of a thermally-conductive material;
   a heat source is connected to said heat jacket;
   said heat source operable to increase the temperature of said heat jacket; whereby said heat jacket is operable to radiate heat from a jacket interior wall to a sample cup exterior wall.

9. The apparatus of claim 7, wherein:
   said jacket interior wall surface coated with a coating having an emissivity coefficient in a range of 0.60 to 1.00.

10. The apparatus of claim 7, wherein:
    said cup exterior wall surface coated with a coating having an emissivity coefficient in a range of 0.60 to 1.00.

11. The apparatus of claim 7, wherein:
    said jacket interior wall surface coated with a non-reflective coating.

12. The apparatus of claim 7, wherein:
    said cup exterior wall surface coated with a non-reflective coating.

13. The apparatus of claim 7, wherein:
    said jacket interior wall surface having a finish roughness in a range of 630 to 9,842.5 rms microns (16 to 250 rms micro-inch); and
    said sample cup operable to rotate within said jacket interior wall surface.

14. The apparatus of claim 7, wherein:
    said cup exterior wall surface having a finish roughness in a range of 630 to 9,842.5 rms microns (16 to 250 rms micro-inch); and
    said sample cup operable to rotate within said jacket interior wall surface.

15. The apparatus of claim 7, wherein:
    said jacket interior wall surface coated with a coating having an friction coefficient in a range of 0.2 to 0.0.

16. The apparatus of claim 7, wherein:
    said cup exterior wall surface coated with a coating having an friction coefficient in a range of 0.2 to 0.0.

\* \* \* \* \*

UNITED STATES PATENT AND TRADEMARK OFFICE
CERTIFICATE OF CORRECTION

PATENT NO. : 8,739,609 B2  Page 1 of 1
APPLICATION NO. : 12/732680
DATED : June 3, 2014
INVENTOR(S) : Richard Lukay and Jarod Hammar It is certified that error appears in the above-identified patent and that said Letters Patent is hereby corrected as shown below:

In the claims,

Column 5, line 48, that portion of claim 2 reading "conducted" should read --constructed--.

Signed and Sealed this
Eleventh Day of November, 2014

Michelle K. Lee
*Deputy Director of the United States Patent and Trademark Office*